US00PP10907P

United States Patent [19]

Pouw

[11] Patent Number: Plant 10,907

[45] Date of Patent: May 18, 1999

[54] HYBRID TEA ROSE PLANT NAMED 'RUITENOR'

[75] Inventor: A. A. Pouw, De Kwakel, Netherlands

[73] Assignee: De Ruiter's Nieuwe Rozen B.V., De Kwakel, Netherlands

[21] Appl. No.: 08/921,122

[22] Filed: Aug. 29, 1997

[51] Int. Cl.[6] ..... A01H 5/00

[52] U.S. Cl. ..... Plt./135

[58] Field of Search ..... Plt./11, 16, 17, Plt./130, 135, 136

*Primary Examiner*—Howard J. Locker

*Attorney, Agent, or Firm*—Christie, Parker & Hale, LLP

[57] ABSTRACT

A new variety of hybrid tea rose plant producing salmon orange to orange open flowers of good form and suitable for growing under glass.

1 Drawing Sheet

BACKGROUND OF THE INVENTION

The present invention relates to a new and distinct variety of rose plant of the hybrid tea rose class which was created by crossing undistributed, unnamed and unpatented seedlings as seed and pollen parents in De Kwakel, Holland. The varietal denomination of the new variety is 'Ruitenor'. The new variety was isolated and asexually reproduced by budding in the Netherlands.

SUMMARY OF THE INVENTION

Among the novel characteristics possessed by this new variety which distinguish it from its parents and all other varieties of which I am aware are its attractive salmon orange to orange open flowers of good form borne on a floriferous plant with long stems and suitable for production of cut flowers under glass. The new variety has been reproduced through propagation by cuttings, grafting, budding and micropropagation.

Asexual reproduction by budding of the new variety as performed in De Kwakel, Holland, shows that the foregoing and other distinguishing characteristics come true to form and are established and transmitted through succeeding propagations.

BRIEF DESCRIPTION OF ILLUSTRATION

The accompanying illustration shows a typical specimen of the vegetative growth and flower of the new variety depicted in color as nearly true as it is reasonably possible to make the same in a color illustration of this character.

DESCRIPTION OF THE NEW VARIETY

The following is a detailed description of the new variety, with color terminology in accordance with The Royal Horticultural Society Colour Chart (R.H.S.C.C.) and horticultural terminology in accordance with standard terminology used in UPOV-approved horticultural guideline. The terminology used in color descriptions herein refers to plate numbers in the aforementioned color chart. Phenotypic expression may vary depending upon growing condictions under different climate, soil, and cultivation conditions.

Parentage: See and pollen parents are unnamed seedlings.
Class: Hybrid Tea.

The following further horticultural description is based on observations made of specimens grown under glass in De Kwakel, Holland.

Flower

Blooming habit: Nearly continuous; under glass in The Netherlands about 200 stems/m$^2$/year; most stems about 0.8 m to 1 m.

A. Bud:

(1) *Size.*—Medium, about 1 to 1.5 inches long and about 1 inch wide.

(2) *Form.*—Ovate (shape of longitudinal section just before separation of sepals); urn-shaped after sepals part.

(3) *Color.*—As sepals divide, near 24B to 24D with red edge.

(4) *Sepals.*—Short, about same length as bud until petals unfurl; near 146D with light line at center; spread then reflex back.

(5) *Peduncle.*—About 3.5 inches; strength-erect; strong; color-medium green, near 146A to 146B, few hairs or prickles.

Flower: Medium; viewed from above — star-shaped; viewed from side — (a) upper part of fully opened flower, flattened convex; (b) lower part of fully opened flower, concave.

(1) *Size.*—Average size when fully expanded — about 3 to 4 inches.

(2) *Borne.*—Singly, one to a stem.

(3) *Form.*—Pointed center, exhibition type, spiral imbricated, outer petals reflex to points.

(4) *Petalage.*—Fully double, about 33 petals.

(5) *Color.*—After sepals part and petals unfurl color of petal top surface appears near 28A to 28B; petal under surface near 20B; as flower ages the marginal zone of the outer side changes to 38A. Point of petal attachment near 9A. Overall tonality from a distance is attractive orange-yellow bi-color, when the bloom is not fully open. The open bloom would be characterized as salmon-orange to orange.

(6) *Peduncle.*—Slight roughness.

(7) *Fragrance.*—Absent or very weak to weak.

(8) *Length of stems.*—About 25 to 40 inches.

Petals:

(1) *Texture.*—Crisp.

(2) *Appearance.*—Inside velvety and outside satiny.

(3) *Form and size.*—Broad, medium, strong undulation of margin.

(4) *Arrangement.*—Regularly arranged, imbricated.

(5) *Petaloids.*—About 12, most have stripe near 9A.

(6) *Lasting quality.*—About 18 days on plant, but flower color fades, and about 12 days after cutting.

Reproductive Organs

A. Stamens, filaments and anthers:
*Arrangement and color.*—Regularly arranged around styles; color of filaments — yellow.
B. Pollen:
*Color.*—Yellow.
C. Styles: Long, stigma above mouth of receptacle, yellow.
D. Stigmas: Orange, positioned below anthers.
Hip: Funnel-shaped, medium seed vessel at petal fall.

Plant

A. Form: Narrow, bushy, average disease resistance; height about 60 inches (about 70 inches or more under low light conditions), spread about 20 inches.
B. Growth: Vigorous.
C. Foliage: Compound 3, 5 and 7 leaflets.
(1) *Size.*—Medium width and length.
(2) *Quantity.*—Abundant.
(3) *Color.*—Juvenile foliage — under side near 183C, under side near 183A to 183B; weak anthocyanin coloration, (shoot about 20 cm long); mature leaf color — upperside near 131A, underside near 191A.
(4) *Shape.*—Ovate.
(5) *Texture.*—Upper side is dull, underside is matte.
(6) *Edge.*—Serrate.
(7) *Serration.*—Ordinary, acute apices.
(8) *Leaf stem.*—Color — near 137B.
(9) *Stipules.*—Long, simple, medium green, distinct darker green auricle.
(10) *Leaflets.*—Cross section — slight concave: weak undulation of margin; terminal leaflet — medium length and narrow width; blade about 2 to 2.5 inches long and 1 to 2 inches wide, rounded base.
D. Wood:
(1) *New wood.*—Color — young shoots have weak to medium anthocyanin; coloration — near 144B.
(2) *Old wood.*—Color — near 137B.
E. Prickles (thorns):
(1) *Prickles.*—Present; quantity (main stalk) — none to few; upper side near 165A, base near 143C to 143D. Shape of lower side — concave; quantity — short prickles absent or very few to few, long prickles medium.

What is claimed is:

1. A new and distinct rose plant of the variety substantially as shown and described.

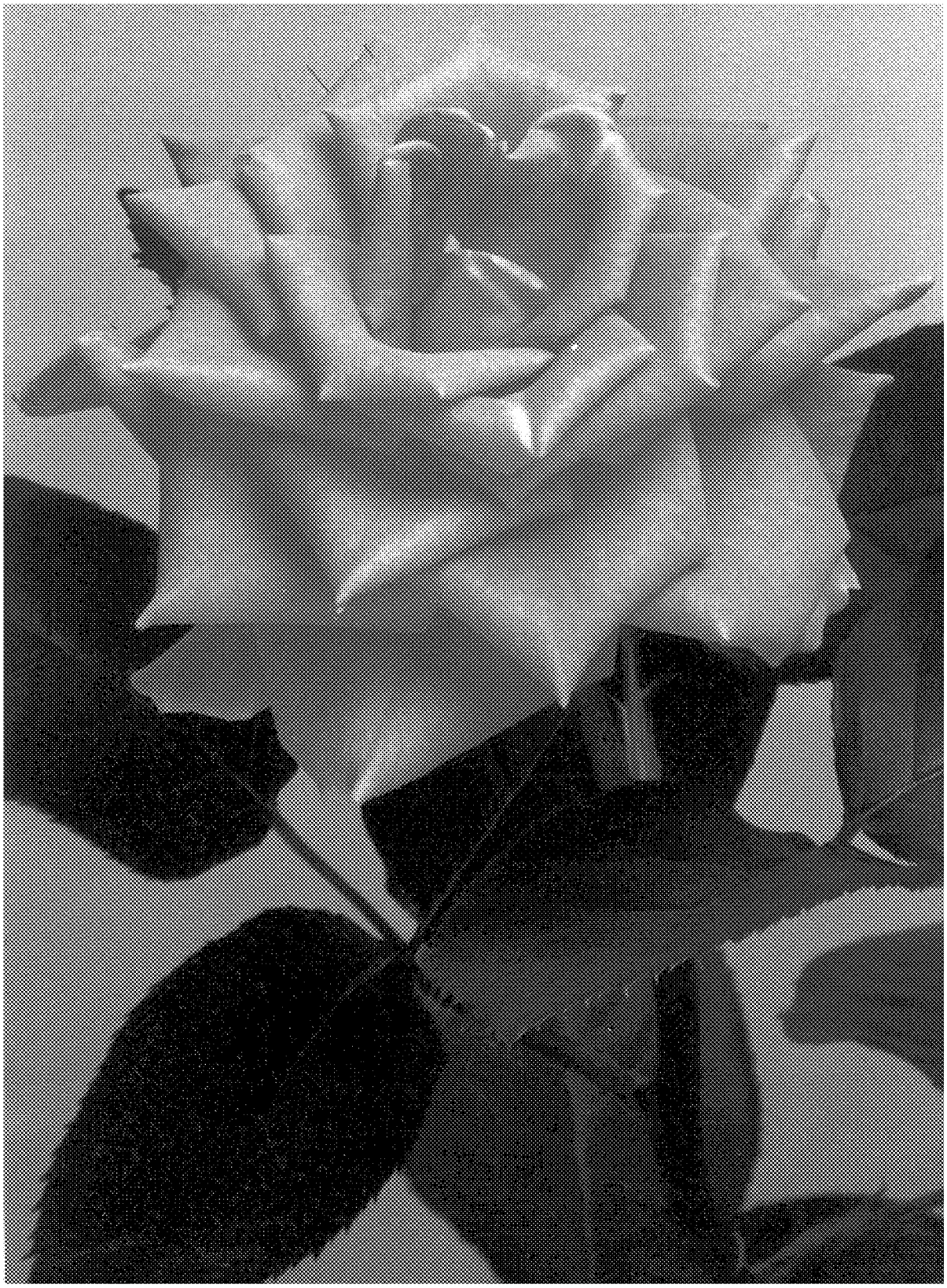

* * * * *